(12) United States Patent
Gil et al.

(10) Patent No.: US 6,562,045 B2
(45) Date of Patent: May 13, 2003

(54) MACHINING APPARATUS

(75) Inventors: Carlos Gil, Sammamish, WA (US); Len Tokish, Issaquah, WA (US)

(73) Assignee: SDGI Holdings, Inc., Memphis, TN (US)

( * ) Notice: Subject to any disclaimer, the term of this patent is extended or adjusted under 35 U.S.C. 154(b) by 0 days.

(21) Appl. No.: 09/934,507

(22) Filed: Aug. 22, 2001

(65) Prior Publication Data

US 2002/0111631 A1 Aug. 15, 2002

Related U.S. Application Data

(63) Continuation-in-part of application No. 09/923,891, filed on Aug. 7, 2001, which is a continuation-in-part of application No. 09/783,860, filed on Feb. 13, 2001, now abandoned.

(51) Int. Cl.[7] .............................................. A61B 17/00
(52) U.S. Cl. ....................................................... 606/79
(58) Field of Search ............................ 606/79, 80, 84, 606/86, 100, 167, 169, 170, 180

(56) References Cited

U.S. PATENT DOCUMENTS

| | | | |
|---|---|---|---|
| 2,677,369 A | 5/1954 | Knowles |
| 3,486,505 A | 12/1969 | Morrison |
| 3,574,374 A | 4/1971 | Keller et al. |
| 3,875,595 A | 4/1975 | Froning |

(List continued on next page.)

FOREIGN PATENT DOCUMENTS

| | | |
|---|---|---|
| DE | 2263842 | 7/1974 |
| DE | 2804936 | 8/1979 |
| DE | 30 23 353 A1 | 4/1981 |
| DE | 37 41 493 A1 | 6/1989 |
| DE | 90 00 094.3 | 4/1990 |
| EP | 0176728 | 4/1986 |
| EP | 00560140 A1 | 9/1993 |
| EP | 196 53 580 | 6/1998 |
| RU | 895433 | 1/1982 |
| RU | 1560184 | 4/1990 |
| WO | WO 00/04839 | 2/2000 |
| WO | WO 00/04851 | 3/2000 |
| WO | WO 00/13619 | 3/2000 |
| WO | WO 00/13620 | 3/2000 |
| WO | WO 02 11633 | 2/2002 |

OTHER PUBLICATIONS

Hawkins et al.; "Shear Stability of an Elastomeric Disk Spacer Within an Intervertebral Joint: A Parametric Study;" Journal of Biomechanical Engineering Technical Briefs; vol. 114; Aug. 1992; pp. 414–415.

Hedman et al.; "Design of an Intervertebral Disc Prosthesis;" Spine; vol. 17; No. 6; 1991; pp. S256–S260.

(List continued on next page.)

*Primary Examiner*—Pedro Philogene
(74) *Attorney, Agent, or Firm*—Haynes and Boone, LLP

(57) ABSTRACT

The invention relates to an apparatus for machining hard tissue and soft tissue associated therewith, having a housing, a rotating shaft having an axis essentially parallel to a longitudinal axis of the apparatus, and adapted to provide power to the apparatus by rotation of the shaft, a drive assembly, having a gear having a rotational axis oriented perpendicular to the longitudinal axis of the apparatus and adapted to mesh with the rotating shaft, a gear hub rigidly attached to the gear, which rotates when the gear rotates, and adapted to attached to a bearing assembly, a bearing assembly having a moveable member rigidly attached to the gear hub, a non-moveable member rigidly attached to the housing, and one or more friction reducing members disposed between the moveable and non-moveable members, and two or more locking members adapted to generate opposing forces helping to hold the drive assembly together, and a cutting element rigidly attached to the drive assembly, wherein the gear hub and bearing assembly are press fit together and the gear and gear hub each comprise complementary interlocking noncircular geometries.

55 Claims, 9 Drawing Sheets

U.S. PATENT DOCUMENTS

| | | |
|---|---|---|
| 3,876,728 A | 4/1975 | Stubstad |
| 4,023,572 A | 5/1977 | Weigand et al. |
| 4,116,200 A | 9/1978 | Braun et al. |
| 4,179,810 A | 12/1979 | Kirsch |
| 4,197,645 A * | 4/1980 | Scheicher .................. 433/128 |
| 4,309,777 A | 1/1982 | Patil |
| 4,349,921 A | 9/1982 | Kuntz |
| 4,599,086 A | 7/1986 | Doty |
| 4,645,507 A | 2/1987 | Engelbrecht et al. |
| 4,714,469 A | 12/1987 | Kenna |
| 4,743,256 A | 5/1988 | Brantigan |
| 4,757,983 A | 7/1988 | Ray et al. |
| 4,759,766 A | 7/1988 | Buettner-Janz et al. |
| 4,759,769 A | 7/1988 | Hedman et al. |
| 4,766,328 A | 8/1988 | Yang |
| 4,777,942 A | 10/1988 | Frey et al. |
| 4,781,072 A * | 11/1988 | Tschudin .................... 74/318 |
| 4,800,639 A | 1/1989 | Frey et al. |
| 4,834,757 A | 5/1989 | Brantigan |
| 4,863,476 A | 9/1989 | Shepperd |
| 4,863,477 A | 9/1989 | Monson |
| 4,874,389 A | 10/1989 | Downey |
| 4,878,915 A | 11/1989 | Brantigan |
| 4,887,595 A | 12/1989 | Heinig et al. |
| 4,904,260 A | 2/1990 | Ray et al. |
| 4,904,261 A | 2/1990 | Dove et al. |
| 4,908,032 A | 3/1990 | Keller |
| 4,908,036 A | 3/1990 | Link et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 4,997,432 A | 3/1991 | Keller |
| 5,002,576 A | 3/1991 | Fuhrmann et al. |
| 5,015,247 A | 5/1991 | Michelson |
| 5,035,716 A | 7/1991 | Downey |
| 5,041,119 A * | 8/1991 | Frigg et al. .................. 606/96 |
| 5,047,055 A | 9/1991 | Bao et al. |
| 5,059,193 A | 10/1991 | Kuslich |
| 5,059,194 A | 10/1991 | Michelson |
| 5,062,845 A | 11/1991 | Kuslich et al. |
| 5,071,437 A | 12/1991 | Steffee |
| 5,080,662 A | 1/1992 | Paul |
| 5,084,048 A | 1/1992 | Jacob et al. |
| 5,108,438 A | 4/1992 | Stone |
| 5,122,130 A | 6/1992 | Keller |
| 5,123,926 A | 6/1992 | Pisharodi |
| 5,171,280 A | 12/1992 | Baumgartner |
| 5,171,281 A | 12/1992 | Parsons et al. |
| 5,176,708 A | 1/1993 | Frey et al. |
| 5,192,326 A | 3/1993 | Bao et al. |
| 5,192,327 A | 3/1993 | Brantigan |
| 5,234,431 A | 8/1993 | Keller |
| 5,236,460 A | 8/1993 | Barber |
| 5,246,458 A | 9/1993 | Graham |
| 5,258,031 A | 11/1993 | Salib et al. |
| 5,261,911 A | 11/1993 | Carl |
| 5,261,913 A | 11/1993 | Marnay |
| 5,306,308 A | 4/1994 | Gross et al. |
| 5,314,477 A | 5/1994 | Marnay |
| 5,314,478 A | 5/1994 | Oka et al. |
| 5,320,644 A | 6/1994 | Baumgartner |
| 5,370,697 A | 12/1994 | Baumigartner |
| 5,383,933 A | 1/1995 | Keller |
| 5,401,269 A | 3/1995 | Bittner-Janz et al. |
| 5,403,314 A | 4/1995 | Currier |
| 5,425,772 A | 6/1995 | Brantigan |
| 5,425,773 A | 6/1995 | Boyd et al. |
| 5,443,514 A | 8/1995 | Steffee |
| 5,456,719 A | 10/1995 | Keller |
| 5,458,638 A | 10/1995 | Kuslich et al. |
| 5,458,642 A | 10/1995 | Beer et al. |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,507,816 A | 4/1996 | Bullivant |
| 5,514,180 A | 5/1996 | Heggeness et al. |
| 5,527,315 A | 6/1996 | Jeanson et al. |
| 5,534,028 A | 7/1996 | Bao et al. |
| 5,534,029 A | 7/1996 | Shima |
| 5,534,090 A | 7/1996 | Navarro et al. |
| 5,545,229 A | 8/1996 | Parsons et al. |
| 5,549,679 A | 8/1996 | Kuslich |
| 5,556,431 A | 9/1996 | Buttner-Janz |
| 5,562,738 A | 10/1996 | Boyd et al. |
| 5,571,189 A | 11/1996 | Kuslich |
| 5,593,409 A | 1/1997 | Michelson |
| 5,609,636 A | 3/1997 | Kohrs et al. |
| 5,645,598 A | 7/1997 | Brosnahan |
| 5,649,926 A | 7/1997 | Howland |
| 5,658,285 A | 8/1997 | Marnay et al. |
| 5,662,158 A | 9/1997 | Caldarise |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,713,899 A | 2/1998 | Marnay et al. |
| 5,716,415 A | 2/1998 | Steffee |
| 5,720,748 A | 2/1998 | Kuslich et al. |
| 5,722,977 A | 3/1998 | Wilhelmy |
| 5,723,013 A | 3/1998 | Jeanson et al. |
| 5,741,253 A | 4/1998 | Michelson |
| 5,782,830 A | 7/1998 | Farris |
| 5,782,832 A | 7/1998 | Larsen et al. |
| 5,797,909 A | 8/1998 | Michelson |
| 5,824,093 A | 10/1998 | Ray et al. |
| 5,824,094 A | 10/1998 | Serhan et al. |
| 5,865,846 A | 2/1999 | Bryan et al. |
| 5,865,848 A | 2/1999 | Baker |
| 5,885,300 A | 3/1999 | Tokuhashi et al. |
| 5,888,197 A | 3/1999 | Mulac et al. |
| 5,888,226 A | 3/1999 | Rogozinski |
| 5,897,087 A | 4/1999 | Farley |
| 5,902,233 A | 5/1999 | Farley et al. |
| 5,928,284 A | 7/1999 | Mehdizadeh |
| 5,947,971 A | 9/1999 | Kuslich et al. |
| 5,976,187 A | 11/1999 | Richelsoph |
| 5,984,865 A | 11/1999 | Farley et al. |
| 5,989,291 A | 11/1999 | Ralph et al. |
| 6,001,130 A | 12/1999 | Bryan et al. |
| 6,017,008 A | 1/2000 | Farley |
| 6,022,376 A | 2/2000 | Assell |
| 6,033,363 A | 3/2000 | Farley et al. |
| 6,059,790 A | 5/2000 | Sand et al. |
| 6,059,829 A | 5/2000 | Schlapfer et al. |
| 6,063,121 A | 5/2000 | Xavier et al. |
| 6,066,174 A | 5/2000 | Farris |
| 6,080,155 A | 6/2000 | Michelson |
| 6,083,228 A * | 7/2000 | Michelson .................. 606/79 |
| 6,086,595 A | 7/2000 | Yonemura et al. |
| 6,096,038 A | 8/2000 | Michelson |
| 6,139,579 A | 10/2000 | Steffee et al. |
| 6,156,067 A | 12/2000 | Bryan et al. |
| 6,162,252 A | 12/2000 | Kuras et al. |
| 6,179,874 B1 | 1/2001 | Cauthen |

| | | | |
|---|---|---|---|
| 6,228,022 B1 | 5/2001 | Friesem et al. | |
| 6,228,026 B1 | 5/2001 | Rull et al. | |
| 6,231,609 B1 | 5/2001 | Mehdizadeh | |
| 6,309,394 B1 * | 10/2001 | Staehlin et al. | 606/79 |
| 2002/0151901 A1 * | 10/2002 | Bryan et al. | 606/80 |

OTHER PUBLICATIONS

Hellier et al.; "Wear Studies for Development of an Intervertebral Disc Prosthesis;" Spine; vol. 17; No. 6 Supplement; 1992; pp. S86–S96.

Hodd; "Far Lateral Lumbar Disc Herniations;" Neurosurgery Clinics of North America; vol. 4, No. 1; Jan. 1993; pp. 117–124.

Langrana et al.; "Finite–Element Modeling of the Synthetic Intevertebral Disc;" Spine; vol. 16; No. 6: 1991; pp. S245–S252.

Lee et al.; "Development of a Prosthetic Intervertebral Disc;" Spine; vol. 16; No. 6; 1991; pp. S253–S255.

Lee et al.; "Natural History & Prognosis of Cervical Spondylosis;" British Medical Journal; Dec. 28, 1963; British Medical Association, London, England; Copyright 1963; pp. 1607–1610.

Long; "Failed Back Surgery Syndrome;" Neurosurgery Clinics of North America, vol. 2, No. 4; Oct. 1991; pp. 899–919.

Ray; "The Artificial Disc—Introduction, History and Socio-economics; " Clinical Efficacy and Outcome in the Diagnosis and Treatment of Low Back Pain; Raven Press, Ltd., NY; 1992; pp. 205–280.

Robinson et al.; The Results of Anterior Interbody Fusion of the Cervical Spine, The Journal of Bone & Joint Surgery; vol. 44–A, No. 8, Dec. 1962; pp. 1569–1587.

Simeone and Rothman; "Cervical Disc Disease;" Pennsylvania Hospital & University of Pennsylvania; 1975; pp. 387–433.

Solini et al.; "Metal Cementless Prosthesis for Vertebral Body Replacement of Metastatic Malignant Disease of the Cervical Spine;" Journal of Spinal Disorders; vol. 2; No. 4; 1989; pp. 254–262.

Taylor, Collier;, "The Occurrence of Optic Neuritis in Lesions of the Spinal Cord, Injury, Tumor, Melitis;" Brain: A Journal of Neurology; vol. 24; Macmillan & Co. Ltd., 1901; pp. 532–550.

Tie–sheng et al.; "Lumbar Intervertebral Disc Prosthesis;" Chinese Medical Journal, 104–(5); 1991; pp. 381–386.

Brain et al.; "The Neurological Manifestations of Cervical Spondylosis;" Brain: A Journal of Neurology, vol. 75; Macmillan & Co.; 1952; pp. 187–225.

Buttner–Janz et al.; "Biomechanics of the SB Charite Lumbar Intervertebral Disc Endoprosthesis;" International Orthopedics; vol. 13; 1989; pp. 173–176.

Edeland; "Some Additional Suggestions for an Intervertebral Disc Prosthesis;" Dept. of Occupational Health; Vdvo PV AB; S–40508; Goteborg; Sweden; 1985 Butterworth & Co. Publishers Ltd.

Enker et al.; "Artifical Disc Replacement;" Spine; vol. 18; No. 8; 1993; pp. 1061–1070.

Artificial Disc, Market Potential and Technology Update, Viscogliosi Bros., LLC, Feb. 2000, pp. 1–65.

Boning–Up, The Musculoskeletal Healthcare Industry, Industry Commentary & Review of 1999, Viscogliosi Bros., LLC, Mar. 10, 2000, pp. 1–33.

Bryan Total Cervical Disc Prosthesis, Single Level Surgical Technique Manual, SPINALdynamics Corporation, 2000, 01080–004, pp. 29.

Spine Industry Dynamics, Viscogliosi Bros., LLC, Mar. 10, 2000, pp. 1–4.

* cited by examiner

MACHINING APPARATUS

This application is a continuation-in-part of U.S. application Ser. No. 09/923,891, filed Aug. 7, 2001, which is a continuation-in-part of U.S. application Ser. No. 09/783,860, filed Feb. 13, 2001 now abandoned, the entire contents of each of which are incorporated herein by reference.

BACKGROUND OF THE INVENTION

1. Field of the Invention

This invention relates generally to machining instruments, and in particular to surgical instruments that are capable of machining hard tissues in relatively confined or constrained environments or spaces, and yet remain reliable for extended periods.

2. Description of Related Art

In a variety of surgical procedures there is a need to machine hard tissues such as bone, i.e. cut, abrade, obliterate or remove hard tissue by mechanical means. In some of these procedures, the human anatomy provides little room to maneuver and properly position a machining instrument. Furthermore, in some procedures precise machining must be done at an angle relative to the direction at which the machining instrument is inserted. These difficulties, caused at least in part by the environment in which the machining instrument is used, create significant design constraints. For example, the components used to make the machining instrument must often be small so that the device can fit into and operate in restricted or constrained anatomical spaces. At the same time, the device may require translational gears to provide the necessary angled machining, which take up much needed space in the instrument. The tension between these conflicting requirements often results in significant design tradeoffs for such equipment.

In addition to meeting these design constraints, the devices must be capable of withstanding the forces exerted on it during repeated uses. These forces may be relatively significant, particularly in view of the size limitations of the components.

Furthermore, in typical surgical machining procedures one must be concerned with the efficiency of the machining operation, and seek to avoid the generation of heat caused by inefficient machining. Excessive heat generation will result in unwanted damage to the living hard tissue and other surrounding tissues in the form of thermal necrosis. In particular, when machining bony tissue, excessive heat can kill osteoblasts in the vicinity of the machining operation, which can lengthen healing times and limit desired bony ingrowth into devices implanted into cavities formed by the machining device. To maximize machining efficiency, the rotational speed and torque of the machining element should be optimized. This often requires a machining instrument design that provides low friction rotation of a machining element at a relatively high speed and torque. Since the instrument must be sized to fit within constrained spaces, little room is available inside the instrument for the gearing, bearing, or other drive mechanisms to enable a low friction, high-speed, high-torque design. Such space constraints are often met by the use of high gear ratios, resulting in suboptimal pinion teeth geometry. The resulting wear significantly limits the life span of such surgical instruments.

In addition, these types of machining instruments are repeatedly exposed to harsh environments that can also shorten their useful life. Specifically, these instruments are often subjected to repeated heat cycles and corrosive cleaning agents during sterilization or autoclaving prior to each use. Therefore, the materials used to fabricate the machining instruments must be biocompatible and capable of withstanding the extreme sterilization temperatures that typically exceed 135° C. In addition, the repeated thermal expansion and contraction of the materials may result in a degradation of some of the mechanical interfaces in the device. As a result, it is desirable to design the devices to minimize such degradation.

One example of this type of device is a milling tool used for the machining of a vertebral body endplate. A vertebral body endplate might be machined in order to prepare the endplate to receive spinal disc prosthesis. An example of procedures for implanting a spinal disc prosthesis is described in U.S. patent application Ser. No. 09/783,860, filed Feb. 13, 2001, and a Continuation-in-part thereof, filed Aug. 7, 2001, the entire contents of each of which are hereby incorporated by reference. In such a procedure the machining instrument must be small enough to be inserted into the intervertebral disc space, which is relatively small. In addition, the machining surface must be positioned at essentially a 90° angle relative to the longitudinal axis of the instrument as it is inserted into the disc space. Consequently, this requires a drive mechanism having relatively small drive components that are capable of milling at approximately 90° relative to the direction the device is inserted. This application thus requires sophisticated instrumentation that is small enough to be maneuvered within constrained spaces in the human body, and yet includes a small and robust drive mechanism capable of facilitating machining at difficult angles and capable of withstanding repeated uses.

Examples of an instrument for machining a vertebral body endplate are described in U.S. Pat. No. 6,083,228. The '228 Patent disclosures does not provide any details on how the device disclosed therein is constructed, and does not address the issues outlined above.

A particular instrument suitable for machining vertebral endplates has been designed and manufactured by Spinal Dynamics Corporation. This design is described in general in U.S. patent application Ser. No. 08/944,234, filed Oct. 6, 1997, and Ser. No. 09/783,860, filed Feb. 13, 2001, and a Continuation-in-part thereof, filed Aug. 7, 2001, the entire contents of each of which are hereby incorporated by reference. The Spinal Dynamics design is shown in FIG. 1 and includes a cutting element 2, a gear 4, and a bearing assembly 6 that are all mounted in a housing 8. In accordance with this design, adhesives are used to secure bearing assembly 6 in housing 8. In addition, gear 4 includes an axial hub 12 that is press fit to an outer gear ring 10. Although this design is effective to machine a vertebral body endplate, the inventors of this application have discovered that, over time, the usefulness of the device may become less reliable. In particular, the repeated use of the device may result in failure of the outer gear ring 10 as a result of the stresses exerted by the press fit of axial hub 12 and/or loads applied during use. In addition, the repeated sterilization of the device may compromise the effectiveness of the adhesives used to secure bearing assembly 6 to the housing. While these instruments are certainly sufficient to achieve a successfull intervertebral implantation, there remains a need for improved instruments that are more durable and can withstand repeated uses.

SUMMARY OF THE INVENTION

The invention relates to an apparatus for machining hard tissue, such as bone, as well as softer tissue associated therewith. The apparatus provides high speed rotation, high torque, and low friction, and is adapted to fit into and operate within small, constrained spaces within anatomical structures of humans or other animals. The apparatus allows for machining tissue from areas and at angles that are difficult for the operator to reach otherwise. The apparatus is robust, and contains components that are capable of withstanding repeated exposure to extreme temperatures as the apparatus is reused, and autoclaved or otherwise heat sterilized prior to each use.

As explained in more detail below, the apparatus takes power supplied by a drive shaft and transfers it approximately 90°, allowing the operator to mill tissue approximately perpendicular to the path of entry of the apparatus into the tissue. This makes the apparatus very suitable for removing tissue from joints. As an example, the apparatus can be used very effectively to remove tissue from vertebral joints, including cortical bone. This might be done in preparing the intervertebral space to receive an implant or prosthesis, for example.

In the apparatus of the invention, power is taken from a rotating shaft, e.g., a geared shaft, having an axis essentially parallel with the longitudinal axis of the apparatus and with the path of entry into the anatomical structure to be machined. The rotating shaft meshes with gear teeth on a perpendicularly oriented gear disposed within a housing on one end of the apparatus. The rotation of this gear also causes the rotation of a gear hub attached to the gear, and which is attached to a moveable member of a bearing assembly. The moveable member of the bearing assembly can move relative to a non-moveable member of the bearing assembly that is affixed to the housing, and is desirably separated from the non-moveable member by one or more friction reducing members. The cutting element of the instrument is attached to the gear or the gear hub, whose rotation causes the cutting element to also rotate. The turning blades of the cutting element can then be brought into contact with the tissue to be removed.

In a particular embodiment, the cutting element can be a cutting disk having axially extending blades or flutes on one side thereof, and an axially extending shaft on the other side, which extends into an axial opening in the gear or gear hub or both, and tightly fits therein.

The gear hub and bearing assembly are desirably press fit together, and the gear and gear hub are desirably fit together by interlocking complementary noncircular geometries, and all three elements are locked together to form a drive assembly which is attached to the housing of the apparatus and to which the cutting element can be removably attached. This locking function may be performed by any suitable mechanism. Desirably, the elements of the drive assembly are locked together with two locking members, one of which is disposed adjacent the gear and the other disposed adjacent the gear hub. These locking members are adapted to generate opposing forces that hold the drive mechanism together, e.g., by generating compressive forces.

The housing of the apparatus contains an opening adapted to receive the drive assembly. This opening contains several different segments, which are generally coaxial, and as explained below, have different diameters to accommodate different portions of the drive assembly.

The invention can be more clearly understood by reference to the attached drawings, the brief description thereof below, and the detailed description of specific embodiments of the invention, all of which are illustrative of, and not limiting of, the invention recited in the appended claims.

DETAILED DESCRIPTION OF SPECIFIC EMBODIMENTS

In general, the present invention provides an apparatus for removing material from the surface of tissue, including hard tissue, such as bone. Preferably, the apparatus is used to form a cavity in a bone surface through a machining process.

The apparatus includes a drive mechanism including a gear, a bearing assembly and a gear hub positioned within a housing, and a cavity forming member mounted on the mounting structure. Preferably the cavity forming member is a machining element, and more preferably it is a bone cutting element. The apparatus includes first means for securing the gear, bearing assembly and gear hub together to form the drive mechanism within an opening in the housing, and second means for securing the machining element to the drive mechanism. In accordance with an embodiment of the present invention, the first means includes a first locking member adjacent the gear and a second locking member adjacent the hub. The first and second locking members provide opposing forces to hold the drive mechanism together.

More specifically, in accordance with an embodiment of the present invention, the housing includes an opening having a first segment having a first diameter, a second segment having a second diameter, and a third segment having a third diameter. The second segment is positioned between the first and third segments. In addition, the first and third diameters are larger than the second diameter.

The gear includes an opening that is substantially centrally located. The gear also includes gear teeth radially spaced around its perimeter. The gear is positioned within the first segment of the housing.

The bearing assembly includes a body having a first portion positioned within the second segment of the housing, and a second portion positioned within the third segment of the housing. The second portion of the body is sized such that it will not pass through the second segment of the housing. The bearing assembly also includes a member that is rotatable relative to the body portion, and that has a channel extending therethrough.

The gear hub is positioned within the gear opening and the channel of the movable member of the bearing assembly. The gear hub includes an enlarged portion adjacent a first end. The enlarged portion is sized such that it will not pass through the channel of the movable member of the bearing assembly. The gear hub further includes a first portion adjacent the enlarged portion that is adapted to interface with the movable member of the bearing assembly such that the two will rotate together. The gear hub also includes a second portion adjacent the first portion that is adapted to interface with the gear opening such that the two will rotate together. Finally, the gear hub includes a third portion adjacent the second portion that is sized such that it will not pass through the gear opening.

Figure 1:
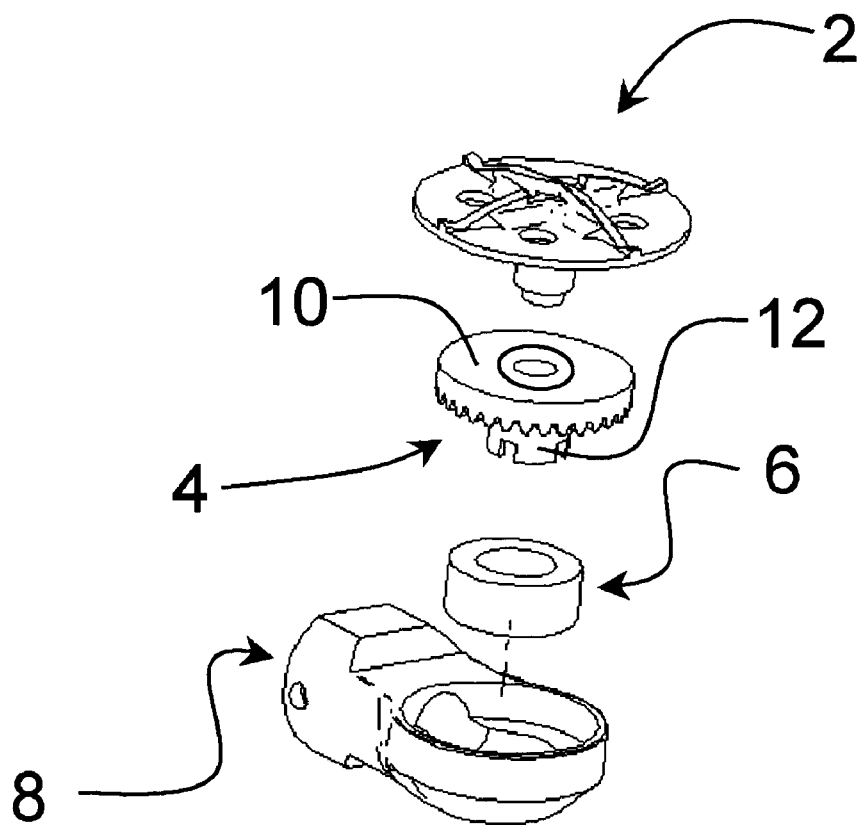
FIG. 1 is an exploded perspective view of an alternative machining apparatus.
Figure 2:
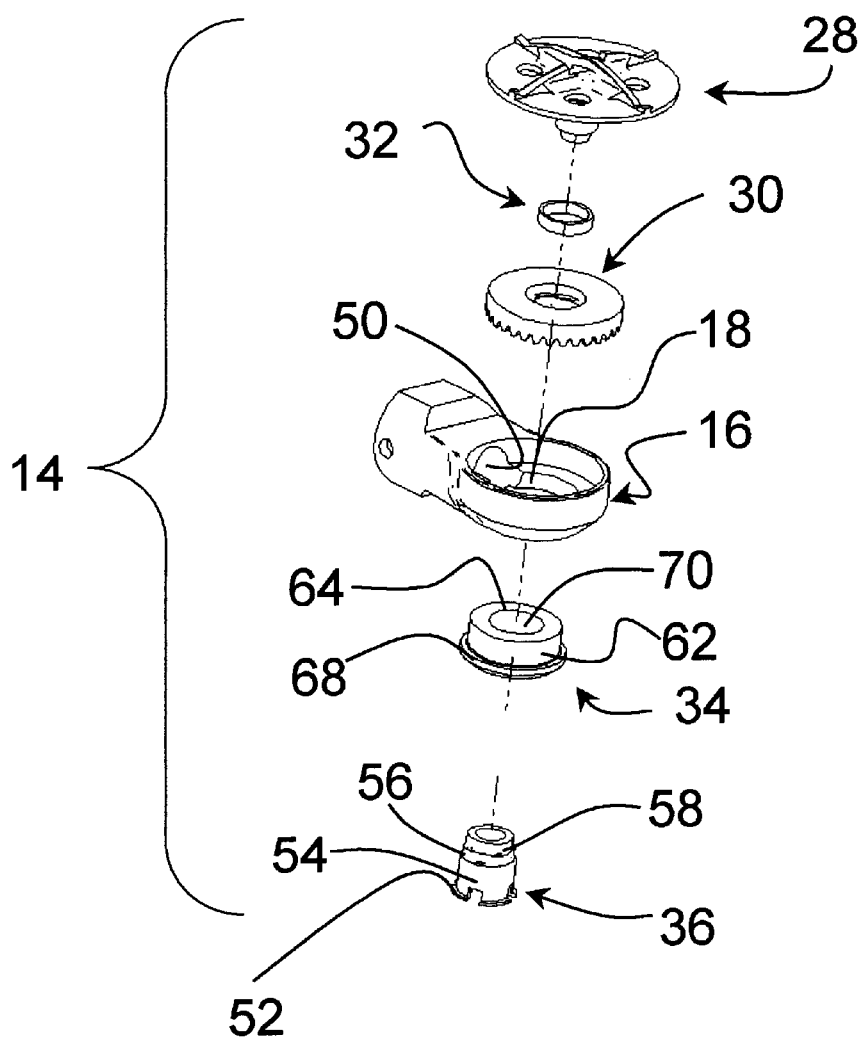
FIG. 2 is an exploded perspective view of one embodiment of a machining apparatus in accordance with the present invention.
Figure 3:
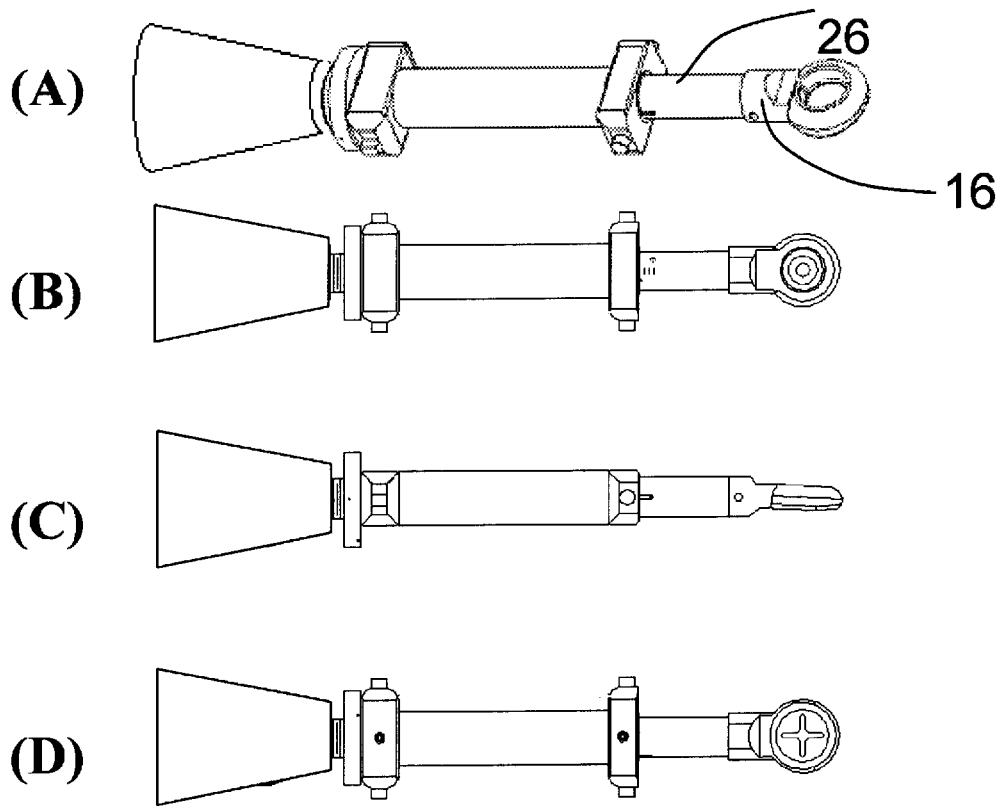
FIG. 3(A) is a perspective view of one embodiment of a machining apparatus in accordance with the present invention and illustrates the device attached to a handle.
FIG. 3(B) is a bottom plan view of the machining apparatus of FIG. 3(A).
FIG. 3(C) is a side plan view of the same machining apparatus.
FIG. 3(D) is a top plan view of the same machining apparatus.
Figure 4:
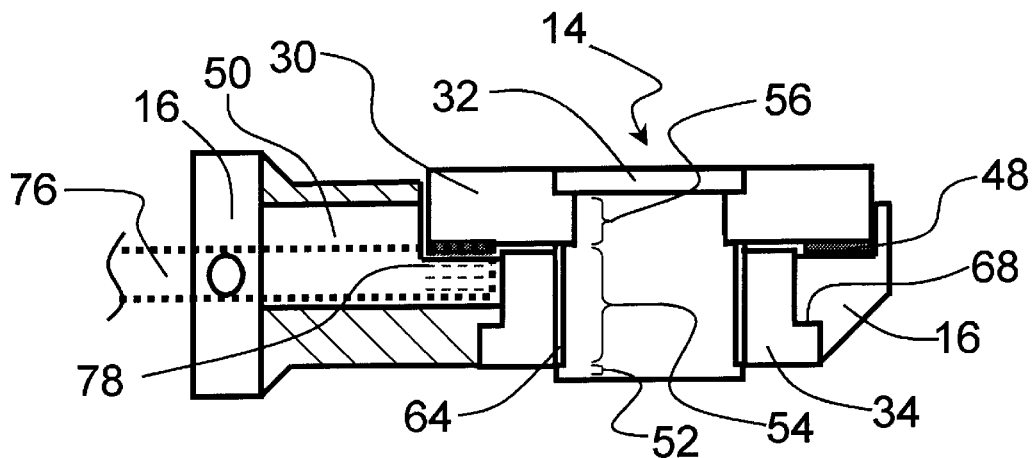
FIG. 4 is a cross sectional schematic view of the machining apparatus shown in FIG. 2 illustrating how the various components are combined.
Figure 5:
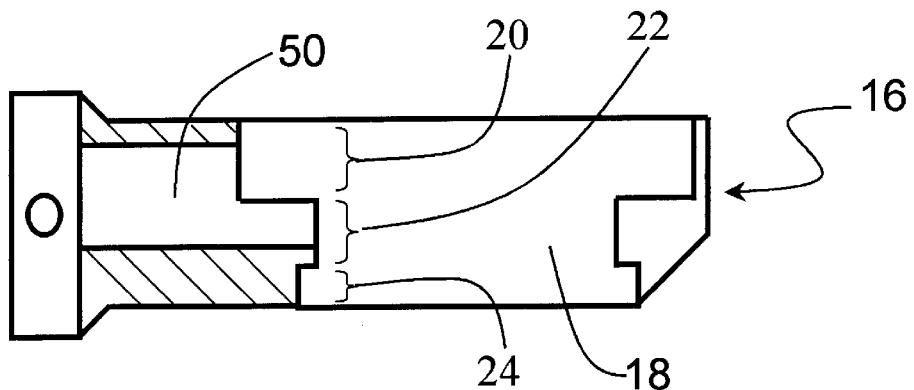
FIG. 5 is a side cross-sectional schematic view of the housing of the machining apparatus shown in FIG. 2.

Preferred embodiments of the present invention will now be described with reference to the Figures. Referring now to FIG. 2, in accordance with a particular embodiment of the present invention, the machining apparatus 14 of the present invention includes a housing 16 having an opening 18 at its distal end and a proximal end adapted to be connected to a handle 26 (see FIG. 3) and a drive mechanism 76 (see FIG. 4). Opening 18 is essentially perpendicular to the longitudinal axis of the machining apparatus 14. As best seen in FIG. 5, opening 18 includes first, second, and third cylindrical segments 20, 22, 24, which are generally coaxial and are adapted to receive a bearing assembly 34 and a gear assembly in the manner described below.

Figure 6:
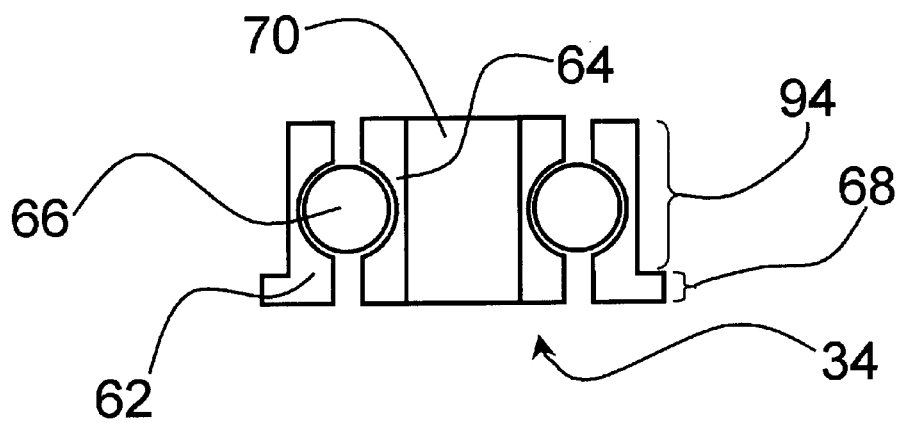
FIG. 6 is a side cross-sectional schematic view of a bearing assembly used in the machining apparatus shown in FIG. 2.

A cross sectional view of bearing assembly 34 is shown in FIG. 6, and generally includes upper portion 94 and lower shoulder portion 68. More specifically, as illustrated, bearing assembly 34 includes outer race 62, inner race 64, balls 66, and gear hub receiving opening 70. Outer race 62 extends along the perimeter of assembly 34. Inner race 64 is centrally positioned within the assembly 34 and extends through both upper portion 94 and lower shoulder portion 68, and preferably extends slightly above outer race 62 as shown in FIG. 6. Inner race 64 is movably attached to assembly 34 such that it may freely rotate relative thereto. The interior surface of inner race 64 defines gear hub receiving opening 70. In accordance with the embodiment illustrated, interior surface of inner race 64 is essentially circular, and opening 70 is thus cylindrical. As described in greater detail below, cylindrical opening 70 is adapted to receive gear hub 36, which interfaces with inner race 64. In accordance with an alternative embodiment, the inner surface of inner race 64 and an outer surface of a portion of gear hub 36 may be non-cylindrical (in the sense that the cross section is not circular) and complementary to facilitate their interfacing with one another.

Figure 7:
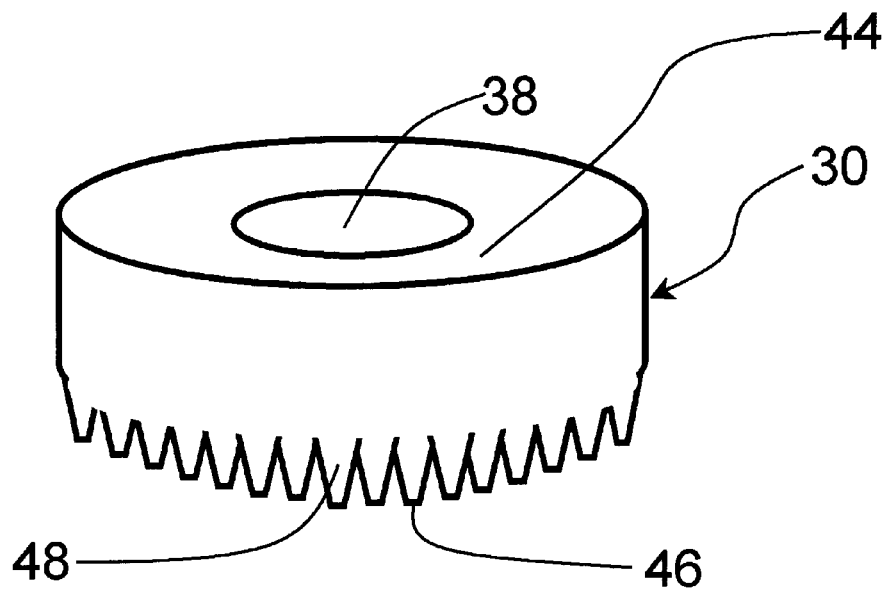
FIG. 7 is a perspective view of a gear used in the machining apparatus shown in FIG. 2.
Figure 8:
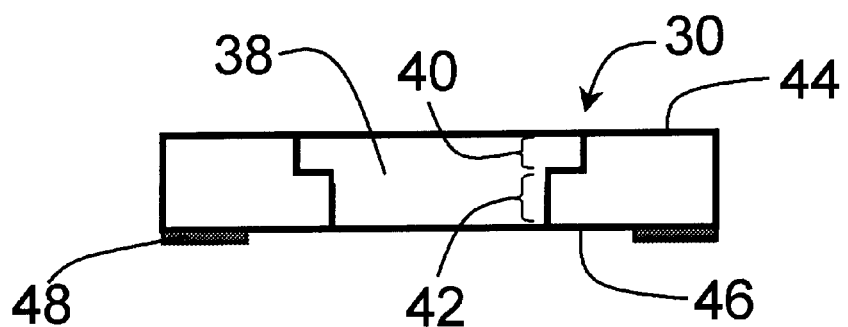
FIG. 8 is a side cross-sectional schematic view of the gear shown in FIG. 7.

In accordance with the embodiment shown in FIG. 2, the gear assembly includes gear 30, gear hub 36 and locking member 32. Referring to FIG. 7 and FIG. 8, a particular embodiment of gear 30 is essentially a circular disk having a central opening 38 extending therethrough. In this embodiment, central opening 38 includes first and second segments 40, 42 along its axis. The first axial segment 40 is generally cylindrical, while the second axial segment 42 can have a non-circular cross-section, e.g. a square cross-section, where the center of the square falls on the axis of the first axial segment 40. Other geometries can also be used for the second axial segment 42, provided that they correspond to the geometry of the gear interfacing segment 56 of the gear hub 36.

As illustrated, the first axial segment 40 has a diameter that is larger than the second axial segment 42. It should be noted that references herein to the diameter of any element having a non-circular geometry refers to the length of any line connecting two points along the perimeter of the element and passing through an approximate center of the element. Thus, reference to cylindrical segment 40 having a diameter greater than square segment 42 means that the length of any line passing through the center of square segment 42 and connecting two perimeter points would be smaller than the diameter of cylindrical segment 40. Conversely, if reference is made herein to a square element having a diameter greater than a circular element, this would only require that at least one line passing through the center of the square element and connecting two perimeter points be greater than the diameter of the circular element.

The upper surface 44 of the gear 30 is essentially flat. The lower surface 46 of the gear 30 includes gear teeth 48 circumferentially spaced thereabout and radially extending near the edge of the disk. Gear teeth 48 are adapted to interface with a drive shaft 76 (as shown in FIG. 4) having mating gear teeth 78 at its distal end. The drive shaft 76 is preferably positioned within a second opening 50 extending longitudinally through the housing 16 (see FIG. 4). The drive shaft 76 is positioned within second opening 50 such that the drive shaft's distal end extends into opening 18.

Figure 9:
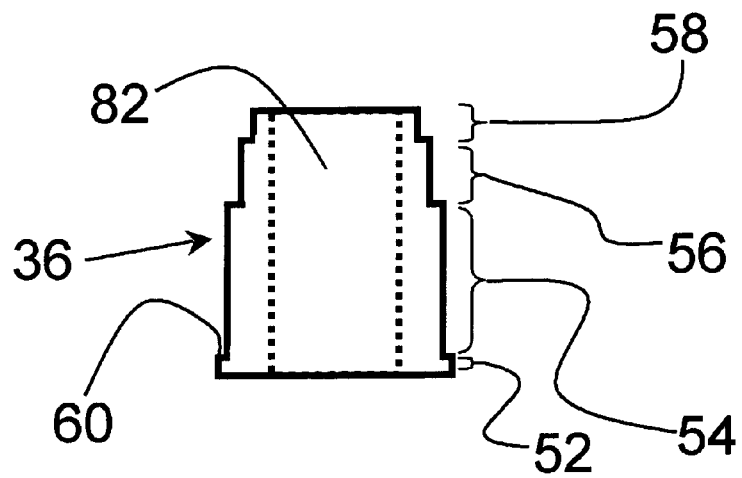
FIG. 9 is a side cross-sectional schematic view of the gear hub shown in FIG. 2.

Referring now to FIG. 2 and FIG. 9, gear hub 36 is generally a hollow tubular member designed to support gear 30 and interface with bearing assembly 34. A preferred embodiment of gear hub 36 includes four segments—shoulder segment 52, bearing interfacing segment 54, gear interfacing segment 56, and locking member interfacing segment 58. Shoulder segment 52 extends around the base of gear hub 36. Bearing interfacing segment 54 extends from shoulder segment 52 and has an outer diameter that is less than the outer diameter of shoulder segment 52, thereby defining shoulder lip 60 at the interface of the two segments.

Bearing interfacing segment 54 is adapted to interface with gear hub receiving opening 70 in bearing assembly 34 such that when the two components are assembled gear hub 36 and inner race 64 rotate in unison. In the embodiment illustrated in FIG. 2, the outer surface of bearing interfacing segment 54 and the inner surface of inner race 64 (which defines gear hub receiving opening 70) are both circular. In accordance with this embodiment the outer diameter of bearing interfacing segment 54 is slightly larger than the diameter of opening 70, and the two components are assembled by press fitting them together. Alternatively, the two components may have noncircular mating geometries that enable them to rotate in unison when they are assembled. In such an alternative embodiment the components may also be sized such that they must be assembled by press fitting, which would further facilitate their rotation together. However, press fitting is not essential. In this embodiment, inner race 64 can desirably have a circular outer geometry that interfaces with bearings 66.

Gear interfacing segment 56 of gear hub 36 extends from bearing interfacing segment 54, and is adapted to be inserted into gear opening 38. Gear interfacing segment 56 has an outer geometry that is sized and shaped to complement the size and shape of a portion of gear opening 38. As noted above, opening 38 includes first and second segments 40, 42 along its axis. Each segment has different geometric characteristics. The geometry of gear interfacing segment 56 preferably complements the size and shape of second axial segment 42 of gear opening 38. In the embodiment illustrated in FIG. 2, the complementary geometry is noncircular, and is substantially square. In addition, gear interfacing segment 56 may be sized to require press fitting into second axial segment 42 of opening 38. The difference in the geometric dimensions of these components, however, must be small enough to avoid excessive loads on the gear when they are press fit together. In accordance with an embodiment of the present invention, the difference in diameters is less than approximately 0.0010 inches, and may also be greater than 0.00005 inches. In accordance with a preferred embodiment this difference is between 0.0002–0.0003 inches.

Locking member interfacing segment 58 of gear hub 36 extends from gear interfacing segment 56. Locking member interfacing segment 58 is adapted to receive locking member 32. In particular, locking member 32 may be any type of mechanical interfacing lock that can be securely affixed to locking member interfacing segment 58, and which is adapted to interface with second axial segment 42 of gear opening 38, as is described in greater detail below.

Gear hub 36 further includes a central opening 82 for receiving the shaft 80 of a cutting element 28. Central opening 82 extends through each of the hub's four segments, and may be threaded along a portion thereof to facilitate securing cutting element shaft 80 to hub 36. Preferably, the threads are directed opposite the direction in which cutting element 28 will turn during use. This will resist a tendency for the cutting element to counter rotate and spiral out of opening 82 during use. In accordance with a preferred embodiment, cutting element 28 will turn in a counter clockwise direction and right-hand threads are included along the cutting element shaft 80 with mating threads included along the hub central opening 82.

In accordance with the preferred embodiment illustrated in FIG. 2, the various components of the present invention are assembled as follows. The upper end of the gear hub 36 (i.e., the end where the hub locking member interfacing segment 58 is located) is positioned within the gear hub receiving opening 70 of the bearing assembly 34. The gear hub 36 and bearing assembly 34 are then press fit together such that bearing inner race 64 is positioned about the hub's bearing interfacing segment 54, and the hub shoulder lip 60 abuts the bottom surface of the inner race 64 as shown in FIG. 4. The gear hub 36/bearing assembly 34 components are then positioned within housing opening 18. In particular, the upper end of gear hub 36 is positioned within the bottom of housing opening 18 (i.e. the end adjacent the third axial segment 24 of opening 18) such that (1) bearing shoulder portion 68 is positioned within the third axial segment 24 of opening 18, (2) the bearing upper portion 94 is positioned within the second axial segment 22 of opening 18, and (3) the hub gear interfacing segment 56 and the hub locking member interfacing segment 58 extend into first axial segment 20 of opening 18.

Gear 30 can then be inserted into the opposite end of housing opening 18 with gear lower surface 46 facing downward or in towards the opening 18. Gear 30 is positioned within opening 18 such that gear opening 38 is positioned around gear hub 36. In particular, gear 30 is placed such that gear interfacing segment 56 of hub 36 is positioned within the second axial segment 42 of gear opening 38, and the hub locking member interfacing segment 58 extends into the first axial segment 40 of gear opening 38.

Locking member 32 may then be positioned on the assembly to secure the various components together. In accordance with a preferred embodiment, locking member 32 is a ring member formed from a shape memory alloy. Locking member 32 is placed within the first axial segment 40 of gear opening 38, and is positioned over the locking member interfacing segment 58 of gear hub 36. Heat is then applied to locking member 32, thereby causing it to shrink and form a secure fit over locking member interfacing segment 58 of gear hub 36. Suitable shape memory alloys for forming locking member 32 include Nitinol. In addition, alternative designs for locking member 32 include any design that provides a secure mechanical interlock between locking member 32 and hub locking member interfacing segment 58. An examples of such a mechanical interlock includes retaining clips and grooves.

The opposing forces of the locking member 32 versus the hub shoulder 52 and bearing shoulder 68 create a secure construct capable of withstanding the various forces that the instrument will encounter through repeated use. In addition, this design also provides the requisite high-speed, high-torque, and low friction machining drive mechanism within the size constraints dictated by the requirement of use in constrained spaces of the human anatomy.

It should be noted that those skilled in the art will appreciate that the order of the steps outlined above is not critical. Alternative sequences for assembling machining apparatus 14 may be used.

Figure 10:
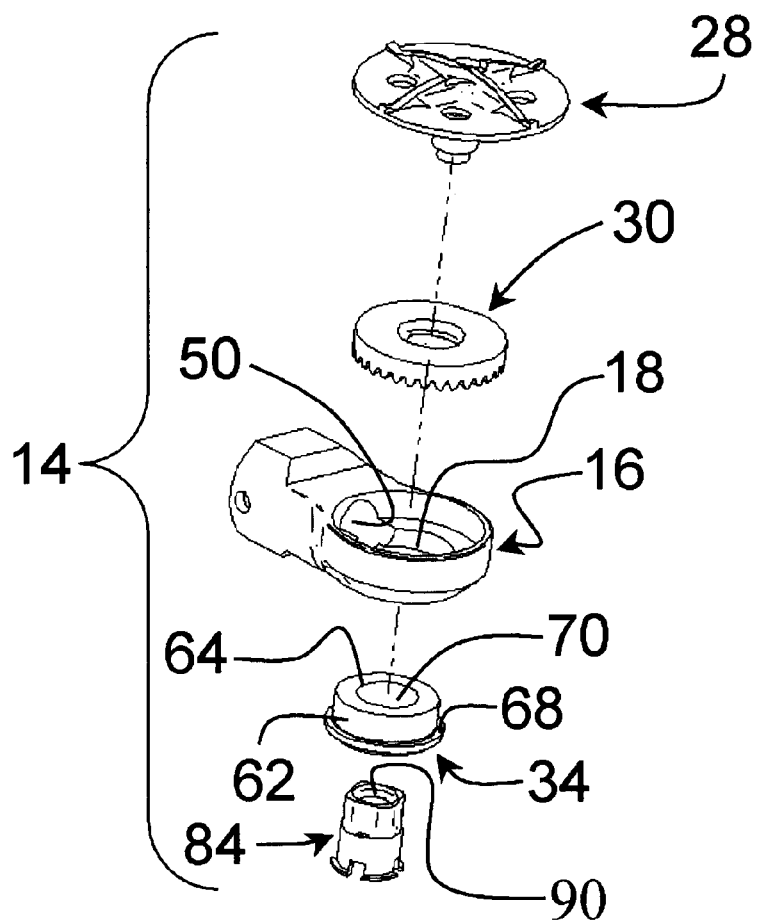
FIG. 10 is an exploded perspective view of another embodiment of a machining apparatus of the present invention.
Figure 11:
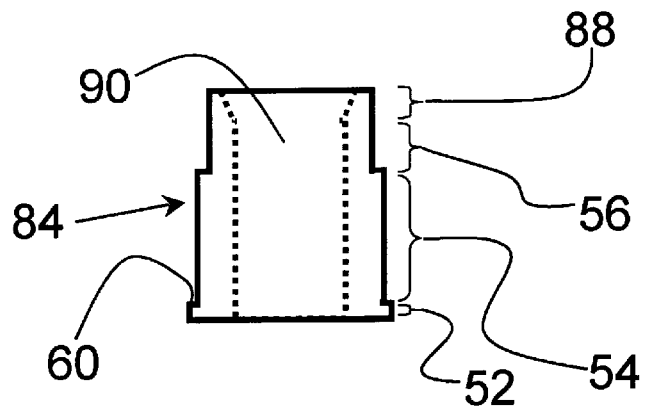
FIG. 11 is a side cross-sectional schematic view of a gear hub used in the embodiment of the machining apparatus shown in FIG. 10.
Figure 12:
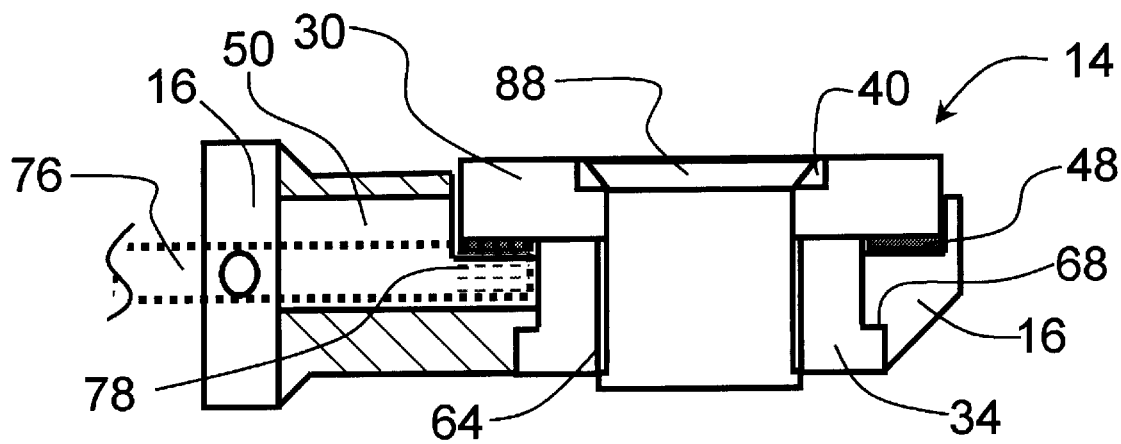
FIG. 12 is a cross sectional schematic view of the embodiment of machining apparatus shown in FIG. 10 illustrating how the various components are combined.

An alternative embodiment of the present invention is illustrated in FIG. 10, FIG. 11, and FIG. 12. In this embodiment the housing 16, cutting element 28, gear 30, and bearing assembly 34 are essentially the same as described above regarding the embodiment shown in FIG. 2. In this alternative embodiment, however, a different gear hub 84 is used. Gear hub 84 is generally a hollow tubular member, and includes an opening 90 passing therethrough. As shown in FIG. 11, a particular embodiment of gear hub 84 includes four segments, three of which are identical to corresponding segments in hub 36 shown in FIG. 9. Those three segments include shoulder segment 52, bearing interfacing segment 54, and gear interfacing segment 56. The fourth segment of gear hub 84 is expandable locking segment 88.

Expandable locking segment 88 extends from gear interfacing segment 56, and is adapted to expand to provide a locking mechanism to secure the various components of the present invention together. In particular, as best illustrated in FIG. 11, expandable locking segment 88 has essentially the same outer geometric profile as gear interfacing segment 56. However, the geometry of opening 90 changes along expandable locking segment 88. As shown, the diameter of opening 90 increases along expandable locking segment 88 toward the end thereof, and the thickness of the material forming hollow tubular hub 84 decreases in this direction. This decrease in thickness facilitates the permanent deformation of expandable locking segment 88, so that after deformation, at least a portion of its outer diameter is greater than the outer diameter of gear interfacing segment 56 and/or second axial segment 42 of gear opening 38 (see FIG. 12). The deformation may be done by any known technique. For example, the deformation may be done by swaging, wherein the expandable locking segment 88 is deformed by pressing the segment with a stainless steel ball. Alternatively, expandable locking segment 88 may be adapted to expand in other ways. For example, the segment may be adapted for deformation by virtue of the material selected to form the hub or the locking segment. Alternatively, the segment may be adapted for deformation by using other geometric configurations that facilitate the deformation, such as scored segments, or a plurality of partial segments.

In use, the housing 16, cutting element 28, gear 30, and bearing assembly 34 are assembled in the same manner described above with regard to the embodiment shown in FIG. 2 such that expandable locking segment 88 extends into first axial segment 40 of gear opening 38. The assembly is then secured together by expanding expandable locking segment 88 until a portion of its diameter is larger than the diameter of second axial segment 42 of gear opening 38.

Figure 13:
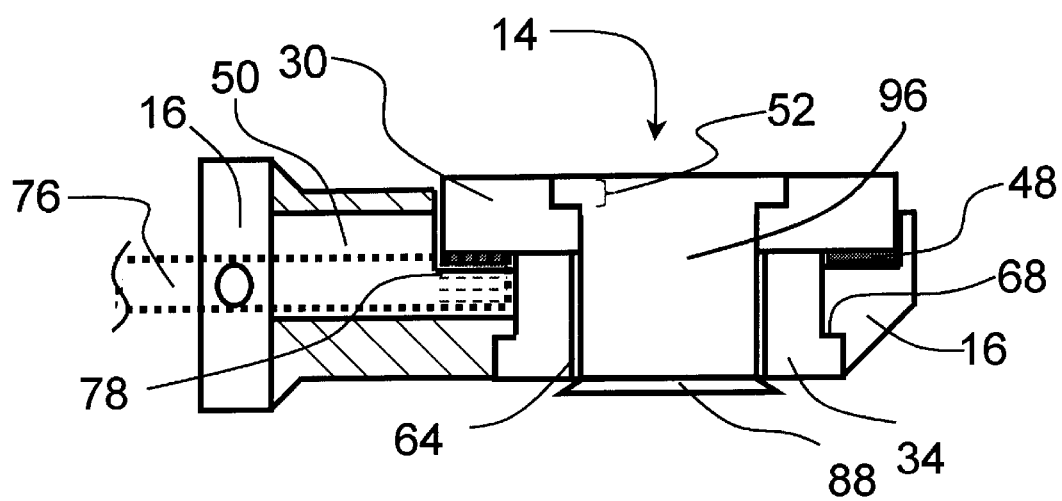
FIG. 13 is a cross sectional schematic view of another embodiment of machining apparatus illustrating how the various components are combined.

Yet another embodiment of the present invention is illustrated in FIG. 13. In accordance with this embodiment, the machining apparatus 14 is essentially identical to the embodiment shown in FIG. 10 except for the gear hub. The embodiment illustrated in FIG. 13 includes gear hub 96.ABear hub 96 is similar in design to gear hub 84 shown in FIG. 10, however the locations of the hub shoulder segment 52 and the expandable locking segment 88 are reversed.

The embodiment shown in FIG. 13 is assembled as follows. The lower end of the gear hub 96 (i.e., the end where expandable locking segment 88 is located) is inserted into gear opening 38 in the side of gear opening 38 facing gear upper surface 44. Gear hub 96 is positioned within gear opening 38 such that hub shoulder segment 52 is positioned within the first axial segment 40 of gear opening 38, gear interfacing segment 56 of hub 96 is positioned within the second axial segment 42 of gear opening 38, and hub bearing interfacing segment 54 and hub expandable locking segment 88 extend below gear lower surface 46. In accordance with this embodiment, hub shoulder segment 52 has an outer geometry having a diameter along a portion thereof that is greater than the diameter of the second axial segment 42 of gear opening 38. This prevents hub 96 from passing completely through gear opening 38.

The gear 30 and gear hub 96 combination is then inserted into housing opening 18. In particular, the lower end of gear hub 96 is inserted into the upper end of opening 18 (i.e., the end adjacent first axial segment 20). The gear 30/gear hub 96 combination is positioned within housing opening 18 such that gear 30 is positioned within the first axial segment 20 of housing opening 18, and hub bearing interfacing segment 54 and expandable locking segment 88 extend into the second axial segment 22 and the third axial segment 24 of opening 18.

The bearing assembly 34 is then positioned within the opposite end of housing opening 18 (i.e., the end adjacent third axial segment 24) with bearing upper portion 94 being inserted first. Assembly 34 is positioned such that (1) bearing shoulder portion 68 is positioned within the third axial segment 24 of opening 18, (2) bearing upper portion 94 is positioned within the second axial segment 22 of opening 18, (3) the hub bearing interfacing segment 54 extends into bearing opening 70, and (4) expandable locking segment 88 extends from bearing opening 70 below bearing shoulder portion 68. As with the previous embodiments, a segment of the diameter of bearing shoulder portion 68 is larger than the diameter of the third axial segment 24 of opening 18. As a result, bearing assembly 34 will not pass through housing opening 18. The housing/gear/gear hub/bearing construct can then be secured together by expanding the expandable locking segment 88 in the same manner described above with regard to gear hub 84.

It should be noted that in the embodiment shown in FIG. 13, the various interacting components may include complementary geometries and/or be press fit together in the same manner and to the same extent described above with regard to the other embodiments of the present invention.

Finally, it should be noted that the machining apparatus of the current invention provides a design that can be sized to access restricted or constrained anatomical spaces, and yet provide the low friction rotation of the machining element and the relatively high machining element speed and torque. In particular, the machining apparatus 14 of the current invention is may be sized such that the vertical dimension of the apparatus 14 assembly in the plane illustrated in FIG. 3C is less than or equal to approximately 11 mm, and is preferably less than or equal to approximately 8.5 mm. In addition, the vertical dimension of the apparatus 14 assembly in the plane illustrated in FIG. 3B may be less than approximately 20 mm, and is preferably between 12 mm and 18 mm. In certain applications, e.g., in preparing intervertebral spaces in the lumbar region, the vertical dimension in the plane illustrated in FIG. 3C may vary between about 6 mm and about 16 mm, more particularly around 10 mm. The vertical dimension illustrated in FIG. 3B may vary between about 26 mm and about 36 mm, more particularly about 30 mm. The design also facilitates achieving a machining element speed of about 3000 to about 10,000 rpm, more particularly about 6000 to about 6500 rpm, and a torque of about 5 to about 15 in-oz., more particularly about 10 in-oz.

Furthermore, the present invention provides a machining element design that is adapted to withstand repeated sterilization cycles, and is adapted to be durable and reliable for extended periods. Specifically, the cutting element, gear, gear hub, housing, bearing races and balls are made from stainless steel, and no adhesives are used to hold these components to one another. In addition, press fitting stresses within the design have been minimized, particularly at the critical gear-hub interface.

The particular embodiments of the invention having been described above are not limiting of the present invention, and those of skill in the art can readily determine that additional embodiments and features of the invention are within the scope of the appended claims and equivalents thereto.

We claim:

1. An apparatus for removing material from the surface of hard tissue, comprising:
    a housing having:
        an opening therein, wherein said opening has
            a first segment having a first diameter,
            a second segment having a second diameter, and
            a third segment having a third diameter,
            whereby said second segment is positioned between said first and third segments, and said first and third diameters are larger than said second diameter;
    a gear positioned within said first segment of said housing, said gear having gear teeth and an axial opening extending therethrough;
    a bearing assembly including
        a body having
            a first portion positioned within the second segment of said housing, and
            a second portion positioned within the third segment of said housing, wherein said second portion of said body is sized such that it will not pass through the second segment of said housing, and
a member that is rotatable relative to the body portion and has a channel extending therethrough;
a gear hub positioned within the gear opening and the channel of the movable member of the bearing assembly, said gear hub including
an enlarged portion adjacent a first end, wherein said enlarged portion is sized such that it will not pass through the channel of said movable member of the bearing assembly,
a first portion adjacent said enlarged portion, wherein said first portion is adapted to interface with the movable member of the bearing assembly such that the two will rotate together,
a second portion adjacent said first portion adapted to interface with the gear opening such that the two will rotate together;
a third portion adjacent said second portion that is sized such that it will not pass through the gear opening.

2. The apparatus of claim 1 wherein said gear hub further includes a opening extending through said first, second and third portions and said opening is at least partially threaded, and said apparatus further includes a cutting element having a threaded shafted adapted to interface with the threaded opening of said gear hub.

3. The apparatus of claim 1 wherein said gear hub includes a central opening adapted to receive a shaft of a machining element.

4. The apparatus of claim 1 wherein said housing has a proximal end and a distal end, and wherein said housing opening is positioned near said distal end and the proximal end adapted to be connected to a handle.

5. The apparatus of claim 4 wherein said housing opening is essentially perpendicular to the longitudinal axis of the apparatus.

6. The apparatus of claim 4 wherein said housing includes a second opening extending from the proximal end to said first opening, and wherein the gear is essentially a disk and the gear teeth are circumferentially spaced thereabout and radially extending near the edge of the disk, whereby the gear teeth are adapted to interface with a drive shaft positioned within the second opening.

7. The apparatus of claim 1 wherein said first, second, and third segments of the housing opening are generally cylindrical and generally coaxial.

8. The apparatus of claim 1 wherein said first portion of said gear hub and the channel in said movable member are cylindrical, and the diameter of said first portion is larger than the diameter of said channel prior to their being assembled together.

9. The apparatus of claim 1 wherein said first portion of said gear hub and the channel in said movable member have non-cylindrical complementary geometries.

10. The apparatus of claim 1 wherein said second portion of said gear hub and the gear opening have non-cylindrical complementary geometries.

11. The apparatus of claim 1 wherein the diameter of said second portion of said gear hub is larger than the diameter of the gear opening by less than approximately 0.0010 inches.

12. The apparatus of claim 1 wherein the diameter of said second portion of said gear hub is larger than the diameter of the gear opening by between approximately 0.00005 and approximately 0.0010 inches.

13. The apparatus of claim 1 wherein the diameter of said second portion of said gear hub is larger than the diameter of the gear opening by between approximately 0.0002 and approximately 0.0003 inches.

14. The apparatus of claim 1 wherein said third portion of said gear hub includes a locking member.

15. The apparatus of claim 14 wherein said locking member is a Nitinol ring.

16. The apparatus of claim 1 wherein said third portion of said gear hub comprises a section that was expanded after the gear, the gear hub, the bearing assembly, and the housing were assembled.

17. The apparatus of claim 1 wherein said enlarged portion of said gear hub includes a locking member.

18. The apparatus of claim 17 wherein said locking member is a Nitinol ring.

19. The apparatus of claim 1 wherein said enlarged portion of said gear hub comprises a section that was expanded after the gear, the gear hub, the bearing assembly, and the housing were assembled.

20. The apparatus of claim 1 wherein said apparatus has a first dimension that is less than or equal to approximately 11 mm, and a second dimension that is less than or equal to approximately 20 mm.

21. The apparatus of claim 20 wherein said first dimension is less than or equal to approximately 8.5 mm.

22. The apparatus of claim 20 wherein said second dimension is between approximately 12 mm and approximately 18 mm.

23. The apparatus of claim 1 wherein said apparatus has a dimension that is less than or equal to approximately 11 mm.

24. The apparatus of claim 1 wherein said apparatus has a dimension that is less than or equal to approximately 20 mm.

25. An apparatus for forming a cavity in a bone surface comprising:
a machining element,
a housing,
a gear,
a bearing assembly,
a gear hub,
first means for securing the gear, bearing assembly and gear hub together to form a drive mechanism within an opening in the housing, and
second means for securing the machining element to the drive mechanism;
wherein said first means includes a first locking member adjacent said gear and a second locking member adjacent said hub, whereby said first and second locking members provide opposing forces to hold the driving mechanism together.

26. The apparatus of claim 25 wherein said second means comprises a threaded shaft extending from said machining element and a correspondingly threaded opening extending into said drive mechanism.

27. The apparatus of claim 25, wherein the first locking member, second locking member, or both, comprise a locking ring.

28. The apparatus of claim 27, wherein the locking ring comprises a shape memory alloy.

29. The apparatus of claim 28, wherein the shape memory alloy is Nitinol.

30. The apparatus of claim 25, wherein the gear hub comprises:
an enlarged portion adjacent a first end, wherein said enlarged portion is sized such that it will not pass through the channel of said movable member of the bearing assembly, a first portion adjacent said enlarged portion, wherein said first portion is adapted to interface with the movable member of the bearing assembly such that the two will rotate together, a second portion adjacent said first portion adapted to interface with the gear opening such that the two will rotate together;

a third portion adjacent said second portion that is sized such that it will not pass through the gear opening.

31. The apparatus of claim 30, wherein said gear hub further includes a opening extending through said first, second and third portions and said opening is at least partially threaded, and said apparatus further includes a cutting element having a threaded shafted adapted to interface with the threaded opening of said gear hub.

32. The apparatus of claim 25, wherein said gear hub includes a central opening adapted to receive a shaft of the machining element.

33. The apparatus of claim 25, wherein said housing comprises:

an opening therein, wherein said opening has
a first segment having a first diameter,
a second segment having a second diameter, and
a third segment having a third diameter,
whereby said second segment is positioned between said first and third segments, and said first and third diameters are larger than said second diameter.

34. The apparatus of claim 33, wherein said housing has a proximal end and a distal end, and wherein said housing opening is positioned near said distal end and the proximal end adapted to be connected to a handle.

35. The apparatus of claim 34, wherein said housing opening is essentially perpendicular to the longitudinal axis of the apparatus.

36. The apparatus of claim 34, wherein said housing includes a second opening extending from the proximal end to said first opening, and wherein the gear is a disk and the gear teeth are circumferentially spaced thereabout and radially extending near the edge of the disk, whereby the gear teeth are adapted to interface with a drive shaft positioned within the second opening.

37. The apparatus of claim 33, wherein said first, second, and third segments of the housing opening are generally cylindrical and generally coaxial.

38. The apparatus of claim 30, wherein the bearing assembly comprises a channel extending therethrough.

39. The apparatus of claim 38, wherein the first portion of the gear hub and the channel of the bearing assembly are each cylindrical, and wherein the diameter of said first portion is larger than the diameter of said channel prior to their being assembled together.

40. The apparatus of claim 38, wherein said first portion of said gear hub and the channel in said movable member have non-cylindrical complementary geometries.

41. The apparatus of claim 30, wherein the gear comprises an axial opening extending therethrough.

42. The apparatus of claim 41, wherein said second portion of said gear hub and the gear opening have non-cylindrical complementary geometries.

43. The apparatus of claim 41, wherein the diameter of said second portion of said gear hub is larger than the diameter of the gear opening by less than approximately 0.0010 inches.

44. The apparatus of claim 43, wherein the diameter of said second portion of said gear hub is larger than the diameter of the gear opening by between approximately 0.00005 and approximately 0.0010 inches.

45. The apparatus of claim 44, wherein the diameter of said second portion of said gear hub is larger than the diameter of the gear opening by between approximately 0.0002 and approximately 0.0003 inches.

46. The apparatus of claim 30, wherein said third portion of said gear hub comprises a section that was expanded after the gear, the gear hub, the bearing assembly, and the housing were assembled.

47. The apparatus of claim 30, wherein said enlarged portion of said gear hub comprises a section that was expanded after the gear, the gear hub, the bearing assembly, and the housing were assembled.

48. The apparatus of claim 25, wherein said apparatus has a first dimension that is less than or equal to approximately 11 mm, and a second dimension that is less than or equal to approximately 20 mm.

49. The apparatus of claim 48, wherein the first dimension is the thickness of the apparatus, measured between the outer edge of the machining element and the opposite edge of the housing.

50. The apparatus of claim 49, wherein the second dimension is the width of the apparatus, measured across the machining element.

51. The apparatus of claim 48, wherein said first dimension is less than or equal to approximately 8.5 mm.

52. The apparatus of claim 48, wherein said second dimension is between approximately 12 mm and approximately 18 mm.

53. The apparatus of claim 25, wherein said apparatus has a dimension that is less than or equal to approximately 11 mm.

54. The apparatus of claim 25, wherein said apparatus has a dimension that is less than or equal to approximately 20 mm.

55. An apparatus for machining hard tissue and soft tissue associated therewith, comprising:

a housing;

a rotating shaft having an axis essentially parallel to a longitudinal axis of the apparatus, and adapted to provide power to the apparatus by rotation of the shaft;

a drive assembly, comprising:
a gear having a rotational axis oriented perpendicular to the longitudinal axis of the apparatus and adapted to mesh with the rotating shaft;
a gear hub rigidly attached to the gear, which rotates when the gear rotates, and adapted to attached to a bearing assembly;
a bearing assembly having a moveable member rigidly attached to the gear hub, a non-moveable member rigidly attached to the housing, and one or more friction reducing members disposed between the moveable and non-moveable members;
two or more locking members adapted to generate opposing forces helping to hold the drive assembly together; and a cutting element rigidly attached to the drive assembly;

wherein the gear hub and bearing assembly are press fit together and the gear and gear hub each comprise complementary interlocking noncircular geometries.

* * * * *